United States Patent [19]

Cottens et al.

[11] Patent Number: 5,665,772
[45] Date of Patent: Sep. 9, 1997

[54] O-ALKYLATED RAPAMYCIN DERIVATIVES AND THEIR USE, PARTICULARLY AS IMMUNOSUPPRESSANTS

[75] Inventors: Sylvain Cottens, Witterswil; Richard Sedrani, Basel, both of Switzerland

[73] Assignee: Sandoz Ltd., Basel, Switzerland

[21] Appl. No.: 416,673

[22] PCT Filed: Sep. 24, 1993

[86] PCT No.: PCT/EP93/02604

§ 371 Date: Apr. 7, 1995

§ 102(e) Date: Apr. 7, 1995

[87] PCT Pub. No.: WO94/09010

PCT Pub. Date: Apr. 28, 1994

[30] Foreign Application Priority Data

Oct. 9, 1992 [GB] United Kingdom ............... 9221220

[51] Int. Cl.⁶ ............... A61K 31/395; C07D 498/16
[52] U.S. Cl. ............... 514/514; 540/456
[58] Field of Search ............... 540/456; 514/514

[56] References Cited

U.S. PATENT DOCUMENTS

| 5,120,842 | 6/1992 | Failli et al. | 540/542 |
| 5,151,413 | 9/1992 | Caufield et al. | 514/63 |
| 5,258,389 | 11/1993 | Goulet et al. | 514/291 |

*Primary Examiner*—Robert T. Bond
*Attorney, Agent, or Firm*—Robert S. Honor; Melvyn M. Kassenoff; Thomas O. McGovern

[57] ABSTRACT

Novel derivatives of rapamycin, particularly 9-deoxorapamycins, 26-dihydro-rapamycins, and 40-0-substituted and 28,40-0,0-di-substituted rapamycins, are found to have pharmaceutical utility, particularly as an immunosuppressants.

10 Claims, No Drawings

O-ALKYLATED RAPAMYCIN DERIVATIVES AND THEIR USE, PARTICULARLY AS IMMUNOSUPPRESSANTS

This application is a 371 of PCT/EP93/02604, filed Sep. 24, 1993.

This invention comprises novel alkylated derivatives of rapamycin having pharmaceutical utility, especially as immunosuppressants.

Rapamycin is a known macrolide antibiotic produced by *Streptomyces hygroscopicus*, having the structure depicted in Formula A:

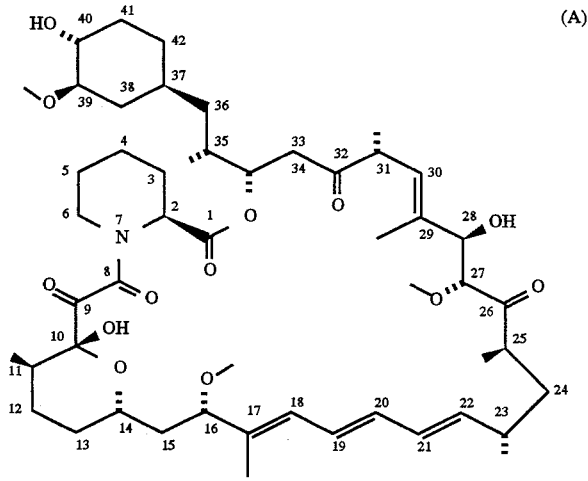

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. Rapamycin is an extremely potent immunosuppressant and has also been shown to have antitumor and antifungal activity. Its utility as a pharmaceutical, however, is restricted by its very low and variable bioavailability as well as its high toxicity. Moreover, rapamycin is highly insoluble, making it difficult to formulate stable galenic compositions.

It has now surprisingly been discovered that certain novel derivatives of rapamycin (the Novel Compounds) have an improved pharmacologic profile over rapamycin, exhibit greater stability and bioavailability, and allow for greater ease in producing galenic formulations. The Novel Compounds are alkylated derivatives of rapamycin having the structure of Formula I:

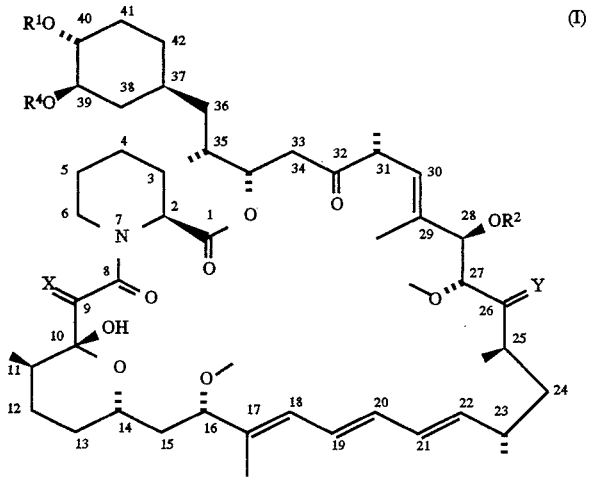

wherein

X is (H,H) or O;
Y is (H,OH) or O;
$R^1$ and $R^2$ are independently selected from H, alkyl, thioalkyl, arylalkyl, hydroxyalkyl, dihydroxyalkyl, hydroxyalkylarylalkyl, dihydroxyalkylarylalkyl, alkoxyalkyl, acyloxyalkyl, aminoalkyl, alkylaminoalkyl, alkoxycarbonylaminoalkyl, acylaminoalkyl, arylsulfonamidoalkyl, allyl, dihydroxyalkylallyl, dioxolanylallyl, carbalkoxyalkyl, and $(R^3)_3Si$ where each $R^3$ is independently selected from H, methyl, ethyl, isopropyl, t-butyl, and phenyl; wherein "alk-" or "alkyl" refers to $C_{1-6}$ alkyl, branched or linear preferably $C_{1-3}$ alkyl, in which the carbon chain may be optionally interrupted by an ether (—O—) linkage; and $R^4$ is methyl, or $R^4$ and $R^1$ together form $C_{2-5}$ alkylene; provided that $R^1$ and $R^2$ are not both H; and provided that where $R^1$ is $(R^3)_3Si$ or carbalkoxyalkyl, X and Y are not both O.

Preferred Novel Compounds include the following:
1. 40-O-Benzyl-rapamycin
2. 40-O-(4'-Hydroxymethyl)benzyl-rapamycin
3. 40-O-[4'-(1,2-Dihydroxyethyl)]benzyl-rapamycin
4. 40-O-Allyl-rapamycin
5. 40-O-[3'-(2,2-Dimethyl-1,3-dioxolan-4(S)-yl)-prop-2'-en-1'-yl]-rapamycin
6. (2'E,4'S)-40-O-(4',5'-Dihydroxypent-2'-en-1'-yl)-rapamycin
7. 40-O-(2-Hydroxy)ethoxycarbonylmethyl-rapamycin
8. 40-O-(2-Hydroxy)ethyl-rapamycin
9. 40-O-(3-Hydroxy)propyl-rapamycin
10. 40-O-(6-Hydroxy)hexyl-rapamycin
11. 40-O-[2-(2-Hydroxy)ethoxy]ethyl-rapamycin
12. 40-O-[(3S)-2,2-Dimethyldioxolan-3-yl]methyl-rapamycin
13. 40-O-[(2S)-2,3-Dihydroxyprop-1-yl]-rapamycin
14. 40-O-(2-Acetoxy)ethyl-rapamycin
15. 40-O-(2-Nicotinoyloxy)ethyl-rapamycin
16. 40-O-[2-(N-Morpholino)acetoxy]ethyl-rapamycin
17. 40-O-(2-N-Imidazolylacetoxy)ethyl-rapamycin
18. 40-O-[2-(N-Methyl-N'-piperazinyl)acetoxy]ethyl-rapamycin
19. 39-O-Desmethyl-39,40-O,O-ethylene-rapamycin
20. (26R)-26-Dihydro-40-O-(2-hydroxy)ethyl-rapamycin
21. 28-O-Methyl-rapamycin
22. 40-O-(2-Aminoethyl)-rapamycin
23. 40-O-(2-Acetaminoethyl)-rapamycin
24. 40-O-(2-Nicotinamidoethyl)-rapamycin
25. 40-O-(2-(N-Methyl-imidazo-2'-ylcarbethoxamido)ethyl)-rapamycin
26. 40-O-(2-Ethoxycarbonylaminoethyl)-rapamycin
27. 40-O-(2-Tolylsulfonamidoethyl)-rapamycin
28. 40-O-[2-(4',5'-Dicarboethoxy-1',2',3'-triazol-1'-yl)-ethyl]-rapamycin The Novel Compounds for immunosuppressive use are preferably the 40-O-substituted rapamycins where X and Y are both O, $R^2$ is H, $R^4$ is methyl, and $R^1$ is other than H; most preferably where $R^1$ is selected from hydroxyalkyl, hydroxyalkoxyalkyl, acylaminoalkyl, and aminoalkyl; especially 40-O-(2-hydroxy)ethyl-rapamycin, 40-O-(3-hydroxy)propyl-rapamycin, 40-O-[2-(2-hydroxy)ethoxy]ethyl-rapamycin, and 40-O-(2-acetaminoethyl)-rapamycin).

Preferably O-substitution at C40 or O,O-disubstitution at C28 and C40 is performed according to the following general process: Rapamycin (or dihydro or deoxorapamycin) is reacted with an organic radical attached to a leaving group (e.g., RX where R is the organic radical, e.g., an alkyl, allyl, or benzyl moiety, which is desired as the O-substituent, and X is the leaving group, e.g., CCl$_3$C(NH)O or CF$_3$SO$_3$) under suitable reaction conditions, preferably acidic or neutral conditions, e.g., in the presence of an acid like trifluoromethanesulfonic acid, camphorsulfonic acid, p-toluenesulfonic acid or their respective pyridinium or substituted pyridinium salts when X is CCl$_3$(NH)O or in the presence of a base like pyridine, a substituted pyridine, diisopropylethylamine or pentamethylpiperidine when X is CF$_3$SO$_3$. O-substituents at C28 only are accomplished in the same manner, but with prior protection at C40. Further modifications are possible. For example, where the substituent is allyl, the isolated, monosubstituted double bond of the allyl moiety is highly amenable to further modification.

The 9-deoxorapamycin compounds are preferably produced by reducing a rapamycin using hydrogen sulfide, by reacting rapamycin with diphenyldiselenide and tributylphosphine or by other suitable reduction reaction.

The 26-dihydro-rapamycins are preferably produced by reducing rapamycins or 9-deoxorapamycins from keto to hydroxy at C26 by a mild reduction reaction, such as a borohydride reduction reaction.

The Novel Compounds are particularly useful for the following conditions:

a) Treatment and prevention of organ or tissue transplant rejection, e.g. for the treatment of recipients of e.g. heart, lung, combined heart-lung, liver, kidney, pancreatic, skin or corneal transplants. They are also indicated for the prevention of graft-versus-host disease, such as following bone marrow transplantation.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) Treatment and prevention of asthma.

d) Treatment of multi-drug resistance (MDR). The Novel Compounds suppress P-glycoproteins (Pgp), which are the membrane transport molecules associated with MDR. MDR is particularly problematic in cancer patients and AIDS patients who will not respond to conventional chemotherapy because the medication is pumped out of the cells by Pgp. The Novel Compounds are therefore useful for enhancing the efficacy of other chemotherapeutic agents in the treatment and control of multidrug resistant conditions such as multidrug resistant cancer or multidrug resistant AIDS.

e) Treatment of proliferative disorders, e.g. tumors, hyperproliferative skin disorder and the like.

f) Treatment of fungal infections.

g) Treatment and prevention of inflammation, especially in potentiating the action of steroids.

h) Treatment and prevention of infection, especially infection by pathogens having Mip or Mip-like factors.

i) Treatment of overdoses of FK-506, rapamycin, immunosuppressive Novel Compounds, and other macrophilin binding immunosuppressants.

The invention thus provides the Novel Compounds described herein, for use as novel intermediates or as pharmaceuticals, methods of treating or preventing the above-described disorders by administering an effective amount of Novel Compound to a patient in need thereof, use of a Novel Compound in the manufacture of a medicament for treatment or prevention of the above-described disorders, and pharmaceutical compositions comprising a Novel Compound in combination or association with a pharmaceutically acceptable diluent or carrier.

Most of the Novel Compounds described herein are highly immunosuppressive, especially those Novel Compounds which are O-substituted at C40, and these Novel Compounds are particularly useful in indications a and b, but not in indication i. Those of the Novel Compounds which are less immunosuppressive, especially those which are O-substituted at C28 only, are particularly useful in indications h and i, but are less preferred in indications a or b.

The Novel Compounds are utilized by administration of a pharmaceutically effective dose in pharmaceutically acceptable form to a subject in need of treatment. Appropriate dosages of the Novel Compounds will of course vary, e.g. depending on the condition to be treated (for example the disease type or the nature of resistance), the effect desired and the mode of administration.

In general however satisfactory results are obtained on administration orally at dosages on the order of from 0.05 to 5 or up to 10 mg/kg/day, e.g. on the order of from 0.1 to 2 or up to 7.5 mg/kg/day administered once or, in divided doses 2 to 4× per day, or on administration parenterally, e.g. intravenously, for example by i.v. drip or infusion, at dosages on the order of from 0.01 to 2.5 up to 5 mg/kg/day, e.g. on the order of from 0.05 or 0.1 up to 1.0 mg/kg/day. Suitable daily dosages for patients are thus on the order of 500 mg p.o., e.g. on the order of from 5 to 100 mg p.o., or on the order of from 0.5 to 125 up to 250 mg i.v., e.g. on the order of from 2.5 to 50 mg i.v.

Alternatively and even preferably, dosaging is arranged in patient specific manner to provide pre-determined trough blood levels, e.g. as determined by RIA technique. Thus patient dosaging may be adjusted so as to achieve regular on-going trough blood levels as measured by RIA on the order of from 50 or 150 up to 500 or 1000 ng/ml, i.e. analogously to methods of dosaging currently employed for Ciclosporin immunosuppressive therapy.

The Novel Compounds may be administered as the sole active ingredient or together with other drugs. For example, in immunosuppressive applications such as prevention and treatment of graft vs. host disease, transplant rejection, or autoimmune disease, the Novel Compounds may be used in combination with Ciclosporin, FK-506, or their immunosuppressive derivatives; corticosteroids; azathioprene; immunosuppressive monoclonal antibodies, e.g., monoclonal antibodies to CD3, CD4, CD25, CD28, or CD45; and 7 or other immunomodulatory compounds. For anti-inflammatory applications, the Novel Compounds can be used together with anti-inflammatory agents, e.g., corticosteroids. For anti-infective applications, the Novel Compounds can be used in combination with other anti-infective agents, e.g., anti-viral drugs or antibiotics.

The Novel Compounds are administered by any conventional route, in particular enterally, e.g. orally, for example in the form of solutions for drinking, tablets or capsules or parenterally, for example in the form of injectable solutions or suspensions. Suitable unit dosage forms for oral administration comprise, e.g. from 1 to 50 mg of a compound of the invention, usually 1 to 10 mg. Pharmaceutical compositions comprising the novel compounds may be prepared analogously to pharmaceutical compositions comprising rapamycin, e.g., as described in EPA 0 041 795, which would be evident to one skilled in the art.

The pharmacological activity of the Novel Compounds are demonstrated in, e.g., the following tests:

1. Mixed lymphocyte reaction (MLR)

The Mixed Lymphocyte Reaction was originally developed in connection with allografts, to assess the tissue compatibility between potential organ donors and recipients, and is one of the best established models of immune reaction in vitro. A murine model MLR, e.g., as described by T. Meo in "Immunological Methods", L. Lefkovits and B. Peris, Eds., Academic Press, N.Y. pp. 227–239 (1979), is used to demonstrate the immunosuppressive effect of the Novel Compounds. Spleen cells ($0.5 \times 10^6$) from Balb/c mice (female, 8–10 weeks) are co-incubated for 5 days with $0.5 \times 10^6$ irradiated (2000 rads) or mitomycin C treated spleen cells from CBA mice (female, 8–10 weeks). The irradiated allogeneic cells induce a proliferative response in the Balb/c spleen cells which can be measured by labeled precursor incorporation into the DNA. Since the stimulator cells are irradiated (or mitomycin C treated) they do not respond to the Balb/c cells with proliferation but do retain their antigenicity. The antiproliferative effect of the Novel Compounds on the Balb/c cells is measured at various dilutions and the concentration resulting in 50% inhibition of cell proliferation ($IC_{50}$) is calculated. The inhibitory capacity of the test sample may be compared to rapamycin and expressed as a relative $IC_{50}$ (i.e. $IC_{50}$ test sample/$IC_{50}$ rapamycin).

2. IL-6 mediated proliferation

The capacity of the Novel Compounds to interfere with growth factor associated signalling pathways is assessed using an interleukin-6 (IL-6)-dependent mouse hybridoma cell line. The assay is performed in 96-well microtiter plates. 5000 cells/well are cultivated in serum-free medium (as described by M. H. Schreier and R. Tees in Immunological Methods, I. Lefkovits and B. Pernis, eds., Academic Press 1981, Vol. II, pp. 263–275), supplemented with 1 ng recombinant IL-6/ml. Following a 66 hour incubation in the absence or presence of a test sample, cells are pulsed with 1 µCi (3-H)-thymidine/well for another 6 hours, harvested and counted by liquid scintillation. (3-H)-thymidine incorporation into DNA correlates with the increase in cell number and is thus a measure of cell proliferation. A dilution series of the test sample allows the calculation of the concentration resulting in 50% inhibition of cell proliferation ($IC_{50}$). The inhibitory capacity of the test sample may be compared to rapamycin and expressed as a relative $IC_{50}$ (i.e. $IC_{50}$ test sample/$IC_{50}$ rapamycin).

3. Macrophilin binding assay

Rapamycin and the structurally related immunosuppressant, FK-506, are both known to bind in vivo to macrophilin-12 (also known as FK-506 binding protein or FKBP-12), and this binding is thought to be related to the immunosuppressive activity of these compounds. The Novel Compounds also bind strongly to macrophilin-12, as is demonstrated in a competitive binding assay.

In this assay, FK-506 coupled to BSA is used to coat microtiter wells. Biotinylated recombinant human macrophilin-12 (biot-MAP) is allowed to bind in the presence or absence of a test sample to the immobilized FK-506. After washing (to remove non-specifically bound macrophilin), bound biot-MAP is assessed by incubation with a streptavidin-alkaline phosphatase conjugate, followed by washing and subsequent addition of p-nitrophenyl phosphate as a substrate. The read-out is the OD at 405 nm. Binding of a test sample to biot-MAP results in a decrease in the amount of biot-MAP bound to the FK-506 and thus in a decrease in the OD405. A dilution series of the test sample allows determination of the concentration resulting in 50% inhibition of the biot-MAP binding to the immobilized FK-506 ($IC_{50}$). The inhibitory capacity of a test sample is compared to the $IC_{50}$ of free FK-506 as a standard and expressed as a relative $IC_{50}$ (i.e., $IC_{50}$-test sample/$IC_{50}$-free FK-506).

4. Localized Graft-Versus-Host (GvH) Reaction

In vivo efficacy of the Novel Compounds is proved in a suitable animal model, as described, e.g., in Ford et al, TRANSPLANTATION 10 (1970) 258. Spleen cells ($1 \times 10^7$) from 6 week old female Wistar/Furth (WF) rats are injected subcutaneously on day 0 into the left hind-paw of female (F344×WF)F$_1$ rats weighing about 100 g. Animals are treated for 4 consecutive days and the popliteal lymph nodes are removed and weighed on day 7. The difference in weight between the two lymph nodes is taken as the parameter for evaluating the reaction.

5. Kidney Allograft Reaction in Rat

One kidney from a female fisher 344 rat is transplanted onto the renal vessel of a unilaterally (left side) nephrectomized WF recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the graft recipient is taken as the parameter for a functional graft.

6. Experimentally Induced Allergic Encephalomyelitis (EAE) in Rats

Efficacy of the Novel Compounds in EAE is measured, e.g., by the procedure described in Levine & Wenk, AMER J PATH 47 (1965) 61; McFarlin et al, J IMMUNOL 113 (1974) 712; Borel, TRANSPLANT. & CLIN. IMMUNOL 13 (1981) 3. EAE is a widely accepted model for multiple sclerosis. Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded.

7. Freund's Adjuvant Arthritis

Efficacy against experimentally induced arthritis is shown using the procedure described, e.g., in Winter & Nuss, ARTHRITIS & RHEUMATISM 9 (1966) 394; Billingham & Davies, HANDBOOK OF EXPERIMENTAL PHARMACOL (Vane & Ferreira Eds, Springer-Verlag, Berlin) 50/II (1979) 108–144. OFA and Wistar rats (male or female, 150 g body weight) are injected i.e. at the base of the tail or in the hind paw with 0.1 ml of mineral oil containing 0.6 mg of lyophilized heat-killed Mycobacterium smegmatis. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. $ED_{50}$ is the oral dose in mg/kg which reduces the swelling (primary or secondary) to half of that of the controls.

8. Antitumor and MDR activity

The antitumor activity of the Novel Compounds and their ability to enhance the performance of antitumor agents by alleviating multidrug resistance is demonstrated, e.g., by administration of an anticancer agent, e.g., colchicine or etoposide, to multidrug resistant cells and drug sensitive cells in vitro or to animals having multidrug resistant or drug sensitive tumors or infections, with and without co-administration of the Novel Compounds to be tested, and by administration of the Novel Compound alone.

Such in vitro testing is performed employing any appropriate drug resistant cell line and control (parental) cell line, generated, e.g. as described by Ling et al., J. Cell. Physiol. 83, 103–116 (1974) and Bech-Hansen et al. J. Cell. Physiol. 88, 23–32 (1976). Particular clones chosen are the multidrug resistant (e.g. colchicine resistant) line CHR (subclone C5S3.2) and the parental, sensitive line AUX B1 (subclone AB1 S11).

In vivo anti-tumor and anti-MDR activity is shown, e.g., in mice injected with multidrug resistant and drug sensitive cancer cells. Ehrlich ascites carcinoma (EA) sub-lines resistant to drug substance DR, VC, AM, ET, TE or CC are developed by sequential transfer of EA cells to subsequent generations of BALB/c host mice in accordance with the methods described by Slater et al., J. Clin. Invest, 70, 1131 (1982).

Equivalent results may be obtained employing the Novel Compounds test models of comparable design, e.g. in vitro, or employing test animals infected with drug-resistant and drug sensitive viral strains, antibiotic (e.g. penicillin) resistant and sensitive bacterial strains, anti-mycotic resistant and sensitive fungal strains as well as drug resistant protozoal strains, e.g. Plasmodial strains, for example naturally occurring sub-strains of *Plasmodium falciparum* exhibiting acquired chemotherapeutic, anti-malarial drug resistance.

9. FKBP binding

Certain of the Novel Compounds are not immunosuppressive, particularly those which are O-substituted at C28 only, such as 28-O-methyl-rapamycin. This can be shown in standard in vitro assays in comparison to FK506 and rapamycin. FK506, for example, is known to be a potent inhibitor of IL-2 transcription, as can be shown in an IL-2 reporter gene assay. Rapamycin, although not active in the IL-2 reporter gene assay, strongly inhibits IL-6 dependent T-cell proliferation. Both compounds are very potent inhibitors of the mixed lymphocyte reaction. Nonimmunosuppressivity can also be shown in the in vivo models 1–7 above. Even those Novel Compounds which are not immunosuppressive, however, bind to macrophilin, which confers certain utilities in which nonimmunosuppressivity is an advantage.

Those of the Novel Compounds which bind strongly to macrophilin and are not themselves immunosuppressive can be used in the treatment of overdoses of macrophilin-binding immunosuppressants, such as FK506, rapamycin, and the immunosuppressive Novel Compounds.

10. Steroid potentiation

The macrophilin binding activity of the Novel Compounds also makes them useful in enhancing or potentiating the action of corticosteroids. Combined treatment with the compounds of the invention and a corticosteroid, such as dexamethasone, results in greatly enhanced steroidal activity. This can be shown, e.g., in the murine mammary tumor virus-chloramphenicol acetyltransferase (MMTV-CAT) reporter gene assay, e.g., as described in Ning, et al., *J. Biol. Chem.* (1993) 268: 6073. This synergistic effect allows reduced doses of corticosteroids, thereby reducing the risk of side effects in some cases.

11. Mip and Mip-like factor inhibition

Additionally, the Novel Compounds bind to and block a variety of Mip (macrophage infectivity potentiator) and Mip-like factors, which are structurally similar to macrophilin. Mip and Mip-like factors are virulence factors produced by a wide variety of pathogens, including those of the genera Chlamidia, e.g., *Chlamidia trachomatis;* Neisseria, e.g., *Neisseria meningitidis;* and Legionella, e.g., *Legionella pneumophilia;* and also by the obligately parasitic members of the order Rickettsiales. These factors play a critical role in the establishment of intracellular infection. The efficacy of the Novel Compounds in reducing the infectivity of pathogens which produce Mip or Mip-like factors can be shown by comparing infectivity of the pathogens in cells culture in the presence and absence of the macrolides, e.g., using the methods described in Lundemose, et al., *Mol. Microbiol.* (1993) 7: 777. The nonimmunosuppressive compounds of the invention are preferred for use in this indication for the reason that they are not immunosuppressive, thus they do not compromise the body's natural immune defenses against the pathogens.

The Novel Compounds are also useful in assays to detect the presence or amount of macrophilin-binding compounds, e.g., in competitive assays for diagnostic or screening purposes. Thus, in another embodiment, the invention provides for use of the Novel Compounds as a screening tool to determine the presence of macrophilin-binding compounds in a test solution, e.g., blood, blood serum, or test broth to be screened. Preferably, a Novel Compound is immobilized in microtiter wells and then allowed to bind in the presence and absence of a test solution to labelled macrophilin-12 (FKBP-12). Alternatively, the FKBP-12 immobilized in microtiter wells and allowed to bind in the presence and absence of a test solution to a Novel Compound which has been labelled, e.g., fluoro-, enzymatically- or radio-labelled, e.g., a Novel Compound which has been O-substituted at C40 and/or C28 with a labelling group. The plates are washed and the amount of bound labelled compound is measured. The amount of macrophilin-binding substance in the test solution is roughly inversely proportional to the amount of bound labelled compound. For quantitative analysis, a standard binding curve is made using known concentrations of macrophilin bind compound.

EXAMPLES:

In the following examples, characteristic spectroscopic data is given to facilitate identification. Peaks which do not differ significantly from rapamycin are not included. Biological data is expressed as a relative $IC_{50}$, compared to rapamycin in the case of the mixed lymphocyte reaction (MLR) and IL-6 dependent proliferation (IL-6 dep. prol.) assays, and to FK-506 in the macrophilin binding assay (MBA). A higher $IC_{50}$ correlates with lower binding affinity.

Example 1: 40-O-Benzyl-rapamycin

To a stirred solution of 183 mg (0.200 mmol) of rapamycin in 2.1 mL of 2:1 cyclo-hexane-methylene chloride is added 75 µL (0.402 mmol) of benzyl-trichloroacetimidate, followed by 2.6 µL (29 µmol 15 mol %) of trifluoromethanesulfonic acid whereupon the mixture turned immediately yellow. After 3 h the mixture is diluted with ethyl acetate and quenched with 10% aqueous sodium bicarbonate. The layers are separated and the aqueous layer is extracted twice with ethyl acetate. The combined organic solution is washed with 10% aqueous sodium bicarbonate, dried over anhydrous sodium sulfate, filtered and concentrated under reduced pressure. The residue is purified by column chromatography on silica gel (50:50 hexane-ethyl acetate) to afford 40-O-benzyl-rapamycin as a white amorphous solid: $^1$H NMR (CDCl$_3$) δ0.73 (1H, dd), 1.65 (3H, s), 1.73 (3H, s), 3.12 (4H, s and m), 3.33 (3H, s), 3.49 (3H, s), 4.15 (1H, bd), 4.65 (1H, d), 4.71 (1H, d), 7.22–7.38 (5H, m); MS (FAB) m/z 1026 ([M+Na]$^+$), 972 ([M-OCH$_3$)]$^+$), 954 ([M-(OCH$_3$+H$_2$O)]$^+$).

| MBA (rel. IC50) | 1.8 |
| IL-6 dep. prol. (rel. IC50) | 10 |
| MLR (rel. IC50) | 110 |

Example 2: 40-O-(4'-Hydroxymethyl)benzyl-rapamycin a) 40-O-[4'-(t-Butyldimethylsilyl)oxymethyl]benzyl-rapamycin To a stirred, cooled (−78° C.) solution of 345 μL (2.0 mmol) of triflic anhydride in 5 mL of methylene chloride is added a solution of 504 mg (2.0 mmol) of 4-(t-butyldimethylsilyl)oxymethyl-benzyl alcohol and 820 mg (4.0 mmol) of 2,6-di-t-butyl-4-methyl-pyridine in 5 mL of methylene chloride. The resulting mixture is warmed to −20° C. and stirring is continued at this temperature for 0.5 h. The mixture is then cooled back to −78° C. and a solution of 914 mg (1.0 mmol) of rapamycin in 5 mL of methylene chloride is added. This mixture is allowed to warm to room temperature overnight and is then quenched with 10% aqueous sodium bicarbonate. The layers are separated and the aqueous layer is extracted with ethyl acetate. The combined organic solution is washed with saturated brine, dried over sodium sulfate, filtered under reduced pressure and concentrated. The residue is purified by column chromatography on silica gel (50:50 hexane-ethyl acetate) to afford 40-O-[4'-(t-butyldimethylsilyl)oxymethyl]benzyl-rapamycin a white foam: MS (FAB) m/z 1170 ([M+Na]$^+$), 1098 ([M-(OCH$_3$+H$_2$O)]$^+$).

b) 40-O-(4'-Hydroxymethyl)benzyl-rapamycin

To a stirred, cooled (0° C.) solution of 98 mg (0.093 mmol) of the compound obtained in example 2 in 2 mL of acetonitrile is added 0.2 mL of HF-pyridine. The resulting mixture is stirred for 2 h and quenched with aqueous sodium bicarbonate, then extracted with ethyl acetate. The organic solution is washed with brine, dried over sodium sulfate, filtered and concentrated. The residue is purified by column chromatography on silica gel (20:80 hexane-ethyl acetate) to afford the title compound as a white foam: $^1$H NMR (CDCl$_3$) δ0.73 (1H, dd), 1.65 (3H, s), 1.74 (3H, s), 3.22 (1H, m), 4.67 (4H, m), 7.35 (4H, m); MS (FAB) m/z 1056 ([M+Na]$^+$), 1002 ([M-OCH$_3$]$^+$), 984 ([M-(OCH$_3$+H$_2$O)]$^+$), 966 ([M-(OCH$_3$+2H$_2$O)]$^+$), 934 ([M-(OCH$_3$+CH$_3$OH+2H$_2$O)]$^+$).

| MBA (rel. IC50) | 2.7 |
| IL-6 dep. prol. (rel. IC50) | 3.9 |
| MLR (rel. IC50) | 3 |

Example 3: 40-O-[4'-(1,2-Dihydroxyethyl)]benzyl-rapamycin a) 40-O-[4'-(2,2-Dimethyl-1,3-dioxolan-4-yl)]benzyl-rapamycin In 10 mL of 1:1 cyclohexane-methylene chloride is dissolved 452 mg (1.24 mmol) of 4-(2,2-dimethyl-1,3-dixolan-4-yl)benzyl trichloroacetimidate, followed by 0.14 mL (0.64 mmol) of 2,6-di-t-butylpyridine 56 μL (0.64 mmol) of trifluoromethanesulfonic acid. To this mixture is added a solution of 587 mg (0.64 mmol) of rapamycin in 2 mL of methylene chloride. The reaction is stirred overnight at room temperature and quenched with aqueous sodium bicarbonate. The layers are separated and the aqueous layer is extracted twice with ethyl acetate. The combined organic solution is washed with saturated brine, dried over anhydrous sodium sulfate, filtered and concentrated. The residue is purified by column chromatography on silica gel (50:50 hexane-ethyl acetate) to give 40-O-[4'-(2,2-Dimethyl-1,3-dioxolan-4-yl)]benzyl-rapamycin as a white, amorphous solid: $^1$H NMR (CDCl$_3$) δ0.73 (1H, dd), 1.48 (3H, s), 1.55 (3H, s), 1.65 (3H, s), 1.74 (3H, s), 3.67 (3H, m), 4.28 (1H, dd), 4.62 (1H, d), 4.69 (1H, d), 5.06 (1H, dd), 7.33 (4H, m), MS (FAB) m/z 1126 ([M+Na]$^+$), 1072 ([M-OCH$_3$]$^+$), 1054 ([M-OCH$_3$+H$_2$O)]$^+$), 1014 ([M-(OCH$_3$+CH$_3$COCH$_3$)]$^+$), 996 ([M-(OCH$_3$+H$_2$O+CH$_3$COCH$_3$)]$^+$), 978 ([M-(OCH$_3$+2H$_2$O+CH$_3$COCH$_3$)]$^+$).

b) 40-O-[4'-(1,2-Dihydroxyethyl)]benzyl-rapamycin

To a solution of 90.7 mg (0.08 mmol) of 40-O-[4'-(2,2-Dimethyl-1,3-dioxolan-4-yl)]benzyl-rapamycin in 4 mL of methanol is added 1 mL of 1N aqueous HCl. After 2 h the mixture is quenched with aqueous sodium bicarbonate and extracted twice with ethyl acetate. The organic solution is washed with brine, dried over anhydrous sodium sulfate and concentrated. The residue is purified by column chromatography on silica gel (ethyl acetate) and the title compound is obtained as a white foam: $^1$H NMR (CDCl$_3$) δ0.73 (1H, dd), 1.65 (3H, s), 1.74 (3H, s), 3.70 (4H, m), 4.63 (1H, d), 4.69 (1H, d), 4.80 (1H, dd), 7.33 (4H, m); MS (FAB) m/z 1086 ([M+Na]$^+$), 1032 ([M-OCH$_3$]$^+$), 1014 ([M-OCH$_3$+H$_2$O)]$^+$), 996 ([M-(OCH$_3$+2H$_2$O)]$^+$).

| MBA (rel. IC50) | 0.92 |
| IL-6 dep. prol. (rel. IC50) | 10.5 |
| MLR (rel. IC50) | 22 |

Example 4: 40-O-Allyl-rapamycin

To a stirred, cooled (−78° C.) solution of 0.33 mL (2.01 mmol) of triflic anhydride in 10 mL of methylene chloride is slowly added a solution of 0.14 mL (2.06 mmol) of allyl alcohol and 0.42 g (2.04 mmol) of 2,6-di-t-butyl-4-methyl-pyridine in 5 mL of methylene chloride. The resulting greenish solution is stirred for 1.5 h and a solution of 915 mg (1.00 mmol) of rapamycin and 0.42 g (2.04 mmol) of 2,6-di-t-butyl-4-methyl-pyridine in 5 mL of methylene chloride is added. Stirring is continued for 0.5 h at −78° C. and then the mixture is warmed to room temperature. After one more hour the mixture is quenched with aqueous sodium bicarbonate and the layers are separated. The aqueous layer is extracted twice with ethyl acetate. The combined organic solution is washed with aqueous sodium bicarbonate and brine, dried over anhydrous sodium sulfate, filtered and concentrated. The resulting green oil is purified by column chromatography on silica gel (60:40 hexane-ethyl acetate) to afford the title compound as a colorless, amorphous solid: $^1$H NMR (CDCl$_3$) δ0.72 (1H, dd), 1.65 (3H, s), 1.74 (3H, s), 3.05 (1H, m), 4.13 (2H, bd), 5.14 (2H, m), 5.27 (2H, m), 5.92 (2H, m), MS (FAB) m/z 976 ([M+Na]$^+$), 922 ([M-OCH$_3$]$^+$), 904 ([M-OCH$_3$+H$_2$O)]$^+$), 886 ([M-(OCH$_3$+2H$_2$O)]$^+$), 872 ([M-(2CH$_3$OH+OH)]$^+$), 854 ([M-(OCH$_3$OH+2H$_2$O)]$^+$).

| | |
|---|---|
| MBA (rel. IC50) | 1 |
| IL-6 dep. prol. (rel. IC50) | 8 |
| MLR (rel. IC50) | 260 |

Example 5: 40-O-[3'-(2,2-Dimethyl-1,3-dioxolan-4(S)-yl)-prop-2'-en-1'-yl]-rapamycin To a stirred, cooled (−78° C.) solution of 0.64 g (4.00 mmol) of E-(4S)-4,5-O,O-isopropylidene-pent-2-en-1,4,5-triol and 1.26 g (6.00 mmol) of 2,6-di-t-butyl-4-methyl-pyridine in 20 mL of methylene chloride is added 0.82 mL (5.00 mmol) of triflic anhydride. The resulting mixture is stirred at this temperature for 2 h and a solution of 1.82 g (2.00 mmol) of rapamycin and 1.26 g (6.00 mmol) of 2,6-di-t-butyl-4-methyl-pyridine in 5 mL of methylene chloride is added. The mixture is allowed to gradually warm to room temperature overnight and is then quenched with aqueous sodium bicarbonate. The layers are separated and the aqueous layer is extracted three times with ethyl acetate. The organic solution is washed with aqueous sodium bicarbonate and brine, dried over anhydrous sodium sulfate, filtered and concentrated. The residue is purified by column chromatography on silica gel (40:60 hexane-ethyl acetate) to afford the title compound as a white solid: $^1$H NMR (CDCl$_3$) δ0.72 (1H, dd), 1.38 (3H, s), 1.42 (3H, s), 1.65 (3H, s), 1.73 (3H, s), 3.06 (1H, m), 3.58 (2H, m), 4.08 (1H, dd), 4.15 (2H, m), 4.52 (1H, bdd), 5.72 (1H, m), 5.88 (1H, m); MS (FAB) m/z 1076 ([M+Na]$^+$), 1022 ([M-OCH$_3$]$^+$), 1004 ([M-OCH$_3$+H$_2$O)]$^+$), 964 ([M-(OCH$_3$+CH$_3$COCH$_3$)]$^+$), 946 ([M-(OCH$_3$+H$_2$O+CH$_3$COCH$_3$)]$^+$), 946 ([M-(OCH$_3$+2H$_2$O+CH$_3$COCH$_3$)]$^+$).

| | |
|---|---|
| MBA (rel. IC50) | 0.64 |
| IL-6 dep. prol. (rel. IC50) | 11 |
| MLR (rel. IC50) | 8 |

Example 6: (2'E, 4'S)-40-O-(4,5'-Dihydroxypent-2'-en-1'-yl)-rapamycin

The conditions described in example 3, step b) applied to the compound obtained in the previous example, followed by purification through column chromatography on silica gel (95:5 ethyl acetate-methanol) afford the title compound as a white foam: $^1$H NMR (CDCl$_3$) δ0.68 (1H, dd), 3.04 (1H, m), 4.18 (5H, m), 5.75 (1H, dd), 5.88 (1H, m), MS (FAB) m/z 1036 ([M+Na]$^+$), 1013 (M$^+$), 995 ([M-H$_2$O]$^+$), 982 ([M-OCH$_3$]$^+$), 964 ([M-OCH$_3$+H$_2$O)]$^+$), 946 ([M-(OCH$_3$+2H$_2$O)]$^+$), 832 ([M-(2CH$_3$OH+OH)]$^+$), 914 ([M-(OCH$_3$CH$_3$OH+2H$_2$O)]$^+$).

| | |
|---|---|
| MBA (rel. IC50) | 1.7 |
| IL-6 dep. prol. (rel. IC50) | 12 |
| MLR (rel. IC50) | 3.5 |

Example 7: 40-O-(2-Hydroxy)ethoxycarbonylmethyl-rapamycin a) 40-O-[2-(t-Butyldimethylsilyl)oxy]ethoxycarbonylmethyl-rapamycin To a stirred solution of 2.74 g (3.00 mmol) of rapamycin and 30 mg (0.06 mmol of dirhodium tetraacetate dihydrate in 30 mL of methylene chloride is added a solution of 0.38 mL (3.60 mmol) of 2-(t-butyldimethylsilyl)oxyethyl diazoacetate in 10 ml of methylene chloride over 5 h. After the addition is complete stirring is continued for one more hour, then the reaction is quenched with 1N aq. HCl. The layers are separated and the aqueous layer is extracted with ethyl acetate. The combined organic solution is washed with aq. sodium bicarbonate and brine, dried over anhydrous sodium sulfate, filtered and concentrated. The residue is purified by column chromatography on silica gel (40:60 hexane-ethyl acetate) yielding 40-O-[2-(t-butyldimethylsilyl)oxy]ethoxycarbonylmethyl-rapamycin: $^1$H NMR (CDCl$_3$) δ0.06 (6H, s), 0.68 (1H, dd), 0.88 (9H, s), 1.64 (3H, s), 1.73 (3H, s), 3.12 (5H, s and m), 3.81 (2H, dd), 4.19 (2H, dd), 4.32 (2H, s); MS (FAB) m/z 1152 ([M+Na]$^+$), 1080 ([M-(OCH$_3$+H$_2$O)]$^+$).

b) 40-O-(2-Hydroxy)ethoxycarbonylmethyl-rapamycin

To a stirred, cooled (0° C.) solution of 81 g (0.07 mmol) of 40-O-[2-(t-butyldimethylsilyl)oxy]ethoxycarbonylmethyl-rapamycin in 1.5 mL of acetonitrile is added 0.15 mL of HF-pyridine. After 2 h the reaction is quenched with aq. sodium bicarbonate. The mixture is extracted with ethyl acetate. The organic solution is washed with brine, dried over anhydrous sodium sulfate, filtered and concentrated. The residue is purified by PTLC (ethyl acetate) to afford the title compound as a white solid: $^1$H NMR (CDCl$_3$) δ0.70 (1H, dd), 1.65 (3H, s), 1.75 (3H, s), 3.13 (5H, s and m), 3.85 (3H, m), 4.25 (5H, m); MS (FAB) m/z 1038 ([M+Na]$^+$), 984 ([M-(OCH$_3$]$^+$), 966 ([M-(OCH$_3$+H$_2$O)]$^+$), 948 ([M-(OCH$_3$+2H$_2$O)]$^+$).

| | |
|---|---|
| MBA (rel. IC50) | 4 |
| IL-6 dep. prol. (rel. IC50) | 9.7 |
| MLR (rel. IC50) | 2.1 |

Example 8: 40-O-(2-Hydroxy)ethyl-rapamycin a) 40-O-[2-(t-Butyldimethylsilyl)oxy]ethyl-rapamycin A solution of 9.14 g (10 mmol) of rapamycin and 4.70 mL (40 mmol) of 2,6-lutidine in 30 mL of toluene is warmed to 60° C. and a solution of 6.17 g (20 mmol) of 2-(t-butyldimethylsilyl)oxyethyl triflate and 2.35 mL (20 mmol) of 2,6-lutidine in 20 mL of toluene is added. This mixture is stirred for 1.5 h. Then two batches of a solution of 3.08 g (10 mmol) of triflate and 1.2 mL (10 mmol) of 2,6-lutidine in 10 mL of toluene are added in a 1.5 h interval. After addition of the last batch, stirring is continued at 60° C. for 2 h and the resulting brown suspension is filtered. The filtrate is diluted with ethyl acetate and washed with aq. sodium bicarbonate and brine. The organic solution is dried over anhydrous sodium sulfate, filtered and concentrated. The residue is purified by column chromatography on silica gel (40:60 hexane-ethyl acetate) to afford 40-O-[2-(t-butyldimethylsilyl)oxy]ethyl-rapamycin as a white solid: $^1$H NMR (CDCl$_3$) δ0.06 (6H, s), 0.72 (1H, dd), 0.90 (9H, s), 1.65 (3H, s), 1.75 (3H, s), 3.02 (1H, m); 3.63 (3H, m), 3.72 (3H, m); MS (FAB) m/z 1094 ([M+Na]$^+$), 1022 ([M-(OCH$_3$+H$_2$O)]$^+$).

b) 40-O-(2-Hydroxy)ethyl-rapamycin

To a stirred, cooled (0° C.) solution of 4.5 g (4.2 mmol) of 40-O-[2-(t-butyldimethylsilyl)oxy]ethyl-rapamycin in 20 mL of methanol is added 2 mL of 1N HCl. This solution is stirred for 2 h and neutralized with aq. sodium bicarbonate. The mixture is extracted with three portions of ethyl acetate. The organic solution is washed with aq. sodium bicarbonate and brine, dried over anhydrous sodium sulfate, filtered and concentrated. Purification by column chromatography on silica gel (ethyl acetate) gave the title compound as a white solid: $^1$H NMR (CDCl$_3$) δ0.72 (1H, dd), 1.65 (3H, s), 1.75 (3H, s), 3.13 (5H, s and m), 3.52–3.91 (8H, m); MS (FAB) m/z 980 ([M+Na]$^+$), 926 ([M-(OCH$_3$]$^+$), 908 ([M-(OCH$_3$+H$_2$O)]$^+$), 890 ([M-(OCH$_3$+2H$_2$O)]$^+$), 876 ([M-(2CH$_3$OH+OH)]$^+$), 858 ([M-(OCH$_3$+CH$_3$OH+2H$_2$O)]$^+$).

| | |
|---|---|
| MBA (rel. IC50) | 2.2 |
| IL-6 dep. prol. (rel. IC50) | 2.8 |
| MLR (rel. IC50) | 3.4 |

Example 9: 40-O-(3-Hydroxy)propyl-rapamycin a) 40-O-[3-(t-Butyldimethylsilyl)oxy]propyl-rapamycin The same procedure as described in example 8, step a) using 3-(t-butyldimethylsilyl)oxyprop-1-yl triflate affords 40-O-[3-(t-butyldimethylsilyl)oxy]propyl-rapamycin: $^1$H NMR (CDCl$_3$) δ0.05 (6H, s), 0.72 (1H, dd), 0.90 (9H, s), 1.65 (3H, s), 1.74 (3H, s), 1.77 (2H, m), 3.03 (1H, m), 3.52–3.73 (7H, m); MS (FAB) m/z 1108 ([M+Na]$^+$), 1036 ([M-(OCH$_3$+H$_2$O)]$^+$).

b) 40-O-(3-Hydroxy)propyl-rapamycin

Treatment of the compound obtained in step a) in the conditions described in example 8, step b) yields the title compound: $^1$H NMR (CDCl$_3$) δ0.72 (1H, dd), 1.65 (3H, s), 1.75 (3H, s), 1.80 (2H, m), 3.05 (1H, m), 3.55–3.91 (8H, m); MS (FAB) m/z 994 ([M+Na]$^+$), 940 ([M-(OCH$_3$)]$^+$), 922 ([M-(OCH$_3$+H$_2$O)]$^+$), 904 ([M-(OCH$_3$+2H$_2$O)]$^+$), 872 ([M-(OCH$_3$+CH$_3$OH+2H$_2$O)]$^+$).

| | |
|---|---|
| MBA (rel. IC50) | 1.6 |
| IL-6 dep. prol. (rel. IC50) | 2.7 |
| MLR (rel. IC50) | 11 |

Example 10: 40-O-(6-Hydroxy)hexyl-rapamycin a) 40-O-[6-(t-Butyldimethylsilyl)oxy]hexyl-rapamycin The same procedure as described in example 8, step a) using 6-(t-butyldimethylsilyl)oxyhex-1-yl triflate affords 40-O-[6-(t-Butyldimethylsilyl)oxy]hexyl-rapamycin: MS (FAB) m/z 1150 ([M+Na]$^+$).

b) 40-O-(6-Hydroxy)hexyl-rapamycin

Treatment of the compound obtained in step a) in the conditions described in example 8, step b) yields the title compound: $^1$H NMR (CDCl$_3$) δ0.72 (1H, dd), 1.38 (2H, m), 1.57 (4H, m), 1.65 (3H, s), 1.74 (3H, s), 3.02 (1H, m), 3.49–3.72 (8H, m); MS (FAB) m/z 1036 ([M+Na]$^+$), 982 ([M-(OCH$_3$)]$^+$), 964 ([M-(OCH$_3$+H$_2$O)]$^+$), 946 ([M-(OCH$_3$+2H$_2$O)]$^+$), 914 ([M-(OCH$_3$+CH$_3$OH+2H$_2$O)]$^+$).

| | |
|---|---|
| MBA (rel. IC50) | 0.8 |
| IL-6 dep. prol. (rel. IC50) | 8.5 |
| MLR (rel. IC50) | 18 |

Example 11: 40-O-[2-(2-Hydroxy)ethoxy]ethyl-rapamycin a) 40-O-[2-t-Butyldimethylsilyl)oxyethoxy]ethyl-rapamycin The same procedure as described in example 8, step a) using 2-[2-(t-butyldimethylsilyl)oxy-ethoxy]ethyl triflate affords 40-O-[2-(t-butyldimethylsilyl)oxyethoxy]ethyl-rapamycin: $^1$H NMR (CDCl$_3$) δ0.06 (6H, s), 0.71 (1H, dd), 0.88 (9H, s), 1.65 (3H, s), 1.74 (3H, s), 3.07 (1H, m), 3.51–3.79 (11H, m); MS (FAB) m/z 1138 ([M+Na]$^+$), 1115 (M$^+$), 1097 ([M-H$_2$O]$^+$), 1084 ([M-(OCH$_3$)]$^+$), 1066 ([M-(OCH$_3$+H$_2$O)]$^+$), 1048 ([M-(OCH$_3$+2H$_2$O)]$^+$), 1034 ([M-(2CH$_3$OH+OH)]$^+$), 1016 ([M-(OCH$_3$+CH$_3$OH+2H$_2$O)]$^+$).

b) 40-O-[2-(2-Hydroxy)ethoxy]ethyl-rapamycin

Treatment of the compound obtained in step a) in the conditions described in example 8, step b) yields the title compound: $^1$H NMR (CDCl$_3$) δ0.72 (1H, dd), 1.65 (3H, s), 1.74 (3H, s), 3.05 (1H, m), 3.51–3.77 (11H, m); MS (FAB) m/z 1024 ([M+Na]$^+$), 1001 (M$^+$), 983 ([M-H$_2$O]$^+$), 970 ([M-(OCH$_3$]$^+$), 952 ([M-(OCH$_3$+H$_2$O)]$^+$), 934 ([M-(OCH$_3$+2H$_2$O)]$^+$), 920 ([M-(2CH$_3$OH+OH)]$^+$), 902 ([M-(OCH$_3$+CH$_3$OH+2H$_2$O)]$^+$).

| | |
|---|---|
| MBA (rel. IC50) | 1.2 |
| IL-6 dep. prol. (rel. IC50) | 3.2 |
| MLR (rel. IC50) | 2 |

Example 12: 40-O-[(3S)-2,2-Dimethyldioxolan-3-yl]methyl-rapamycin

The same procedure as described in example 8, step a) using the triflate of glycerol acetonide affords the title compound: $^1$H NMR (CDCl$_3$) δ0.72 (1H, dd), 1.36 (3H, s), 1.42 (3H, s), 1.65 (3H, s), 1.75 (3H, s), 3.06 (1H, m), 3.55 (2H, m), 3.69 (3H, m), 4.06 (1H, dd), 4.26 (1H, m); MS (FAB) m/z 1050 ([M+Na]$^+$), 996 ([M-(OCH$_3$)]$^+$), 978 ([M-(OCH$_3$+H$_2$O)]$^+$), 960 ([M-(OCH$_3$+2H$_2$O)]$^+$).

| | |
|---|---|
| MBA (rel. IC50) | 0.9 |
| IL-6 dep. prol. (rel. IC50) | 8 |
| MLR (rel. IC50) | 290 |

Example 13: 40-O-[(2S)-2,3-Dihydroxyprop-1-yl]-rapamycin

Treatment of the compound obtained in the previous example in the conditions described in example 3 yields the title compound: $^1$H NMR (CDCl$_3$) δ0.72 (1H, dd), 1.65 (3H, s), 1.75 (3H, s), 3.07 (1H, m), 3.68 (8H, m); MS (FAB) m/z 1010 ([M+Na]$^+$), 956 ([M-(OCH$_3$)]$^+$), 938 ([M-(OCH$_3$+H$_2$O)]$^+$), 920 ([M-(OCH$_3$+2H$_2$O)]$^+$), 888 ([M-(OCH$_3$+CH$_3$OH 2H$_2$O)]$^+$).

| | |
|---|---|
| MBA (rel. IC50) | 0.67 |
| IL-6 dep. prol. (rel. IC50) | 9 |
| MLR (rel. IC50) | 10 |

Example 14: 40-O-(2-Acetoxy)ethyl-rapamycin

To a stirred, cooled (0° C.) solution of 53 mg (0.055 mmol) of 40-O-hydroxyethyl-rapamycin in 2 mL of methylene chloride is added 0.2 mL of pyridine followed by 0.02 mL (0.281 mmol) of acetyl chloride. The mixture is stirred for 3 h and diluted with ethyl acetate, then washed with aq. sodium bicarbonate, cold 1N HCl and again with aq. sodium bicarbonate. The organic solution is dried over anhydrous sodium sulfate, filtered and concentrated. The residue is purified by column chromatography on silica gel (30:70 hexane-ethyl acetate) to afford the title compound as a white solid: $^1$H NMR (CDCl$_3$) δ0.72 (1H, dd), 1.65 (3H, s), 1.75 (3H, s), 2.08 (3H, s), 3.07 (1H, m), 3.78 (2H, dd), 4.20 (2H, dd); MS (FAB) m/z 1022 ([M+Na]$^+$), 999 (M$^+$), 982 ([M-(OH]$^+$), 968 ([M-(OCH$_3$)]$^+$), 950 ([M-(OCH$_3$+H$_2$+H$_2$O)]$^+$), 932 ([M-(OCH$_3$+2H$_2$O)]$^+$), 918 ([M-(2CH$_3$OH+OH)]$^+$), 900 ([M-(OCH$_3$+CH$_3$OH+2H$_2$O)]$^+$).

| | |
|---|---|
| MBA (rel. IC50) | 2 |
| IL-6 dep. prol. (rel. IC50) | 7.6 |
| MLR (rel. IC50) | 3.6 |

Example 15: 40-O-(2-Nicotinoyloxy)ethyl-rapamycin

The same procedure as described in the previous example using nicotinoyl chloride hydrochloride affords the title compound: $^1$H NMR (CDCl$_3$) δ0.72 (1H, dd), 1.65 (3H, s), 1.75 (3H, s), 3.07 (1H, m), 3.94 (2H, dd), 4.49 (2H, t), 7.39 (1H, dd), 8.31 (1H,, ddd), 8.78 (1H, ddd), 9.24 (1H, dd); MS (FAB) m/z 1085 ([M+Na]$^+$), 1063 ([M+H]$^+$), 1045

([M-OH]⁺), 1031 ([M-(OCH₃]⁺), 1013 ([M-(OCH₃+H₂O)]⁺).

| MBA (rel. IC50) | 1.1 |
|---|---|
| IL-6 dep. prol. (rel. IC50) | 6.9 |
| MLR (rel. IC50) | 5 |

Example 16: 40-O-[2-(N-Morpholino)acetoxy]ethyl-rapamycin a) 40-O-(2-Bromoacetoxy)ethyl-rapamycin The same procedure as described in example 14 using bromoacetyl chloride affords 40-O-(2-bromoacetoxy)ethyl-rapamycin: ¹H NMR (CDCl₃) δ0.72 (1H, dd), 1.67 (3H, s), 1.76 (3H, s), 3.03 (1H, m), 3.82 (2H, m), 3.87 (2H, s), 4.31 (2H, m); MS (FAB) m/z 1100, 1102 ([M+Na]⁺), 1077 (M⁺), 1061 ([M-H₂O]⁺), 1046, 1048 ([M-(OCH₃]⁺), 1028, 1030 ([M-(OCH₃+H₂O)]⁺), 1012 ([M-(OCH₃+2H₂O)]⁺), 996 ([M-(2CH₃OH+OH)]⁺), 980 ([M-(OCH₃+CH₃OH+2H₂O)]⁺).

b) 40-O-[2-(N-Morpholino)acetoxy]ethyl-rapamycin

To a stirred, cooled (−45° C.) solution of 54 mg (0.05 mmol) of 40-O-(2-bromoacetoxy)ethyl-rapamycin in 0.5 mL of DMF is added a solution of 0.022 mL (0.25 mmol) of morpholine in 0.2 mL of DMF and the resulting mixture is stirred at that temperature for 1 h, then treated with aq. sodium bicarbonate. This mixture is extracted three times with ethyl acetate. The organic solution is washed with brine, dried over anhydrous sodium sulfate, filtered and concentrated. The residue is purified by column chromatography on silica gel (95:5 ethyl acetate-methanol) yielding the title compound as an amorphous white solid: ¹H NMR (CDCl₃) δ0.72 (1H, dd), 1.67 (3H, s), 1.76 (3H, s), 2.60 (3H, m), 3.07 (1H, m), 3.24 (2H, s), 3.78 (8H, m), 4.27 (2H, t); MS (FAB) m/z 1107 ([M+Na]⁺), 1085 ([M+H]⁺), 1067 ([M-OH]⁺), 1053 ([M-(OCH₃]⁺), 1035 ([M-(OCH₃+H₂O)]⁺).

| MBA (rel. IC50) | 1.3 |
|---|---|
| IL-6 dep. prol. (rel. IC50) | 4 |
| MLR (rel. IC50) | 3.5 |

Example 17: 40-O-(2-N-Imidazolylacetoxy)ethyl-rapamycin

The same procedure as described in example 16, step b) using imidazole affords the title compound: ¹H NMR (CDCl₃) δ0.72 (1H, dd), 1.67 (3H, s), 1.78 (3H, s), 3.06 (3H, m), 3.80 (2H, m), 4.32 (2H, m), 4.73 (2H, s), 6.97 (1H, dd), 7.09 (1H, dd), 7.52 (1H, dd); MS (FAB) m/z 1066 ([M+Na]⁺), 1048 ([M+OH]⁺), 1034 ([M-(OCH₃]⁺), 1016 ([M-(OCH₃+H₂O)]⁻).

| MBA (rel. IC50) | 1 |
|---|---|
| IL-6 dep. prol. (rel. IC50) | 7.6 |
| MLR (rel. IC50) | 3.4 |

Example 18: 40-O-[2-(N-Methyl-N'-piperazinyl)acetoxy]ethyl-rapamycin

The same procedure as described in example 16, step b) using N-methylpiperazine affords the title compound: ¹H NMR (CDCl₃) δ0.72 (1H, dd), 1.67 (3H, s), 1.77 (3H, s), 2.78 (4H, s and m), 3.02 (4H, bs), 3.08 (1H, m), 3.32 (2H, s), 3.80 (2H, dd), 4.27 (2H, t); MS (FAB) m/z 1098 ([M+Na]⁺), 1066 ([M-(OCH₃]⁺).

| MBA (rel. IC50) | 2.6 |
|---|---|
| IL-6 dep. prol. (rel. IC50) | 10.3 |
| MLR (rel. IC50) | 5 |

Example 19: 39-O-Desmethyl-39,40-O,O-ethylene-rapamycin

To a stirred, cooled (−20° C.) solution of 48 mg (0.05 mmol) of 40-O-hydroxyethyl-rapamycin and 0.023 mL (0.20 mmol) of 2,6-lutidine in 0.5 mL of methylene chloride is added 0.008 mL (0.05 mmol) of triflic anhydride. The mixture is stirred at this temperature for 2 h, then allowed to warm to room temperature and stirred for one more hour. The reaction is quenched with aq. sodium bicarbonate and the resulting mixture is extracted with three portions of ethyl acetate. The organic solution is washed with brine, dried over anhydrous sodium sulfate, filtered and concentrated. The residue is purified by column chromatography on silica gel (30:70 hexane-ethyl acetate) to afford the title compound as a white solid: ¹H NMR (CDCl₃) δ1.66 (3H, s), 1.75 (3H, s), 3.14 (3H, s), 3.35 (3H, s), 3.76 (4H, s); MS (FAB) m/z 948 ([M+Na]⁺), 925 (M⁺), 908 ([M-OH]⁺), 894 ([M-(OCH₃]⁺), 876 ([M-(OCH₃+H₂O)]⁺), 858 ([M-(OCH₃+2H₂O)]⁺), 844 ([M-(2CH₃OH+OH)]⁺), 826 ([M-(OCH₃+CH₃OH+2H₂O)]⁺).

| MBA (rel. IC50) | 1.6 |
|---|---|
| IL-6 dep. prol. (rel. IC50) | 22.9 |
| MLR (rel. IC50) | 16 |

Example 20: (26R)-26-Dihydro-40-O-(2-hydroxy)ethyl-rapamycin a) (26R)-26-Dihydro-40-O-[2-(t-Butyldimethylsilyloxy)]ethyl-rapamycin In 4.5 mL of 2:1 acetonitrile-acetic acid is dissolved 315 mg (1.2 mmol) of tetramethylammonium-triacetoxyborohydride. The resulting solution is stirred for 1 at room temperature and cooled to −35° C., then 161 mg (0.15 mmol) of 40-O-[2-(t-butyldimethylsilyloxy)]ethyl-rapamycin is added. The resulting mixture is stirred at the same temperature overnight and is quenched by the addition of aq. sodium bicarbonate. The mixture is extracted with three portions of ethyl acetate. The organic solution is washed with aq. sodium bicarbonate, two portions of 30% aq. Rochelle's salt and brine, dried over anhydrous sodium sulfate, filtered and concentrated. The residue is purified by column chromatography on silica gel (40:60 hexane-ethyl acetate) to afford the title compound as a white solid: ¹H NMR (CDCl₃) δ0.06 (6H, s), 0.73 (1H, dd), 0.90 (9H, s), 1.64 (3H, s), 1.67 (3H, s), 3.02 (1H, m), 3.15 (1H, m), 3.64 (3H, m), 3.71 (2H, dd), 3.91 (1H, s); MS (FAB) m/z 1096 ([M+Na]⁺), 1041 ([M-HOCH₃]⁺), 1024 ([M-(OCH₃+H₂O)]⁺), 1006 ([M-(OCH₃+2H₂O)]⁺), 974 ([M-(OCH₃+CH₃OH+2H₂O)]⁺).

| MBA (rel. IC50) | 3.9 |
|---|---|
| IL-6 dep. prol. (rel. IC50) | 53 |
| MLR (rel. IC50) | 18 |

Example 21: 28-O-Methyl-rapamycin

To a stirred solution of 103 mg (0.1 mmol) of 40-O-TBS-rapamycin (obtained by silylation of rapamycin with 1 eq. of TBS triflate in methylene chloride in the presence of 2 eq. of 2,6-lutidine at 0° C.) in 0.5 mL of methylene chloride is added 85.8 mg (0.40 mmol) of proton sponge followed by 44 mg (0.30 mmol) of trimethyloxonium tetrafluoroborate. The resulting brown heterogeneous mixture is stirred overnight, quenched with aq. sodium bicarbonate and extracted with ethyl acetate. The organic solution is washed with 1N HCl, aq. sodium bicarbonate and brine, then dried over anhydrous sodium sulfate, filtered and concentrated. The residue is purified by column chromatography on silica gel (60:40 hexane-ethyl acetate) to afford 40-O-t-butyldimethylsilyl-28-O-methyl-rapamycin. The latter compound is desilylated in the conditions described in example 10, step b) to afford, after PTLC (ethyl acetate), the title compound as a white solid: $^1$H NMR (CDCl$_3$) δ0.70 (1H, dd), 1.68 (6H, 2s), 2.95 (1H, m), 3.13 (3H, s), 3.14 (3H, s), 3.28 (3H, s), 3.41 (3H, s); MS (FAB) m/z 950 ([M+Na]$^+$), 927 (M$^+$), 909 ([M-H$_2$O]$^+$), 896 ([M-OCH$_3$]$^+$), 878 ([M-(OCH$_3$+H$_2$O)]$^+$), 864 ([M-(OCH$_3$+CH$_3$OH)]$^+$), 846 ([M-(2CH$_3$OH+OH)]$^+$), 832 ([M-(OCH$_3$+2CH$_3$OH)]$^+$), 814 ([M-(3CH$_3$OH+OH)]$^+$).

| | |
|---|---|
| MBA (rel. IC50) | 1.58 |
| IL-6 dep. prol. (rel. IC50) | 1240 |
| MLR (rel. IC50) | 1300 |

Example 22: 40-O-(2-aminoethyl)-rapamycin a) 40-O-(2-bromoethyl)-rapamycin

A solution of 914 mg rapamycin in 5 mL toluene containing 0.64 ml of 2,6-lutidine and 1.28 g of 2-bromoethyl triflate is heated at 65° C. for 18 h. The reaction mixture is then cooled to room temperature, poured on 20 ml of a saturated bicarbonate solution and extracted with 3×20 mL ethyl acetate. The organic phases are dried over sodium carbonate and the solvent removed at reduced pressure on the rotary evaporator. The residue is chromatographed on 100 g silica gel, eluting with hexane/ethyl acetate 3/2 to afford 40-O-(2-bromoethyl)-rapamycin as an amorphous solid: MS (FAB) m/z 1044 and 1042 (100%; M+Na); 972 and 970 (55%, M-(MeOH+H2O)).

H-NMR (CDCl3) d: 0.72 (1H, q, J=12 Hz); 3.13 (3H, s); 3.33 (3H, s); 3.45 (3H,s); 3.9 (4H, m); 4.78 (1H, s)

b) 40-O-(2-azidoethyl)-rapamycin

A solution of 2.4 g of 40-O-(2-bromoethyl)-rapamycin in 40 mL DMF is treated with 0.19 g sodium azide at room temperature. After 2 h, the mixture is poured on 100 mL of saturated sodium bicarbonate and extracted with 3×100 mL ethyl acetate. The organic phases are combined, dried over sodium sulfate and the solvent removed under reduced pressure. The crude product is purified by chromatography on silica gel eluting with hexane/ethyl to afford 40-O-(2-azidoethyl)-rapamycin: MS (FAB): 1005 (100%, M+Na); 951 (24%, M-MeOH); 933 (57%, M-(MeOH+H2O)

c) 40-O-(2-aminoethyl)-rapamycin

To a solution of 230 mg 40-O-(azidoethyl)-rapamycin in 3 mL of THF/water 5/1 at room temperature are added 307 mg of triphenylphosphine. The reaction mixture is becomes yellow. After 7 h, the reaction mixture is loaded on x g silica gel and chromatographed with ethyl acetate/methanol/acetic acid 50/50/0.5 to afford the title product in the form of its acetate: MS (FAB) m/z 979 (45%, M+Na); 957 (100% MH); 925 (63%, M-MeOH); 907 (25%, M-(MeOH+H2O)

MBA (rel. IC50): 0.7

IL-6 dep. prol. (rel. IC50): 10

Example 23: 40-O-(2-acetaminoethyl)-rapamycin

To a solution of 101 mg of the acetate of 40-O-(2-aminoethyl)-rapamycin in 2 mL THF are added 0.02 mL pyridine and 0.07 mL acetyl chloride. The reaction mixture is kept at room temperature for 18 h and then poured on 7 mL saturated sodium bicarbonate. The aqueous phase is extracted 3× with 5 mL ethyl acetate, the organic phases are combined and dried over sodium sulfate. The solvent is evaporated and the residue chromatographed on 10 g silica gel eluting first with ethyl acetate followed by ethyl acetate/methanol/acetic acid 50/50/0.5 to afford the title product: MS (FAB) m/z 1021 (20%, M+Na); 967 (28%, M-MeOH); 949 (100%, M-(MeOH+H2O)

H-NMR (CDCl3) d: 0.71 (1H, q, J=12 Hz); 1.98 (3H, s); 3.13 (3H, s); 3.34 (3H, s); 3.44 (3H, s); 4.75 (1H, s)

MBA (rel. IC50): 1.1

IL-6 dep. prol. (rel. IC50): 2.3

Example 24: 40-O-(2-nicotinamidoethyl)-rapamycin 101 mg of 40-O-(2-aminoethyl)-rapamycin acetate are dissolved in 5 ml ethyl acetate and extracted 2× with saturated sodium bicarbonate. The organic phase is dried over sodium sulfate and the solvent evaporated. The residue is dissolved in 2 mL THF and treated with 22 mg DCC and 15 mg nicotinic acid. After 15 h at room temperature the reaction mixture is evaporated and the residue chromatographed on silica gel, eluting with ethyl acetate followed by ethyl acetate/methanol 9/1, to afford the title product: MS (FAB) m/z 1084 (80%, M+Na); 1062 (40%, MH); 1038 (100%, M-MeOH); 1012 (50%, M-(MeOH+H2O)

H-NMR (CDCl3) d: 0.72 (1H, q, J=12 Hz); 3.13 (3H, s); 3.33 (3H, s); 3.37 (3H, s); 7.39 (1H, dd); J=6 Hz, J=8 Hz), 8.19 (1H, d, J=8 Hz); 8.75 (1H, d, J=6 Hz); 9.04 (1H, broad s)

MBA (rel. IC50): 1.2

IL-6 dep. prol. (rel. IC50): 2.8

Example 25: 40-O-(2-(N-Methyl-imidazo-2'-ylcarbethoxamido)ethyl)-rapamycin

To a solution of 30 mg N-methyl-imidazol-2-carboxylic acid in 1 mL DMF are added 58 mg DCC and 58 mg HOBT. After 2 h, 150 mg 40-O-(2-aminoethyl)-rapamycin are added and the reaction mixture is stirred for 18 at room temperature. The suspension is then filtered, the filtrate diluted with 5 mL ethyl acetate and washed with 2×2 mL of a saturated aqueous bicarbonate solution. The organic phase is dried over sodium sulfate and the solvent evaporated under reduced pressure. The residue is chromatographed over 10 silica gel, eluting with hexane/ethyl acetate ¼ and then ethyl acetate to afford the title product:

MS (FAB) m/z 1087 (36%, M+Na); 1065 (57%, MH); 1033 (100%, M-MeOH); 1015 (46%, M-(MeOH+H2O)

H-NMR (CDCl3) d: 0.72 (1H, q, J=12 Hz); 3.13 (3H, s); 3.33 (3H, s); 3.46 (3H, s); 4.03 (3H, s); 6.93 (1H, broad s); 6.98 (1H, broad s); 7.78 (1H, m);

MBA (rel. IC50): 1.1

IL-6 dep. prol. (rel. IC50): 7

Example 26: 40-O-(2-ethoxycarbonylaminoethyl)-rapamycin

A solution of 200 mg 40-O-(2-azidoethyl)-rapamycin in 3 mL THF/water 5/1 is treated with 267 mg triphenylphosphine for 7 h at room temperature. Then 0.4 mL pyridine are added followed by 194 μL ethyl chloroformiate. After 2 h, the reaction mixture is poured on 5 mL ethyl acetate and washed successively with 10 mL saturated sodium bicarbonate, 5 mL water and 5 ml 10% citric acid. The organic phase is dried over sodium sulfate and the solvent evaporated. The residue is chromatographed over 20 g silica gel, eluting with ethyl acetate followed by ethyl acetate/methanol 9/1, to afford the title product.: MS (FAB) m/z 1051 (35%, M+Na); 997 (30%, M-MeOH); 979 (100%, M-(MeOH+H2O)

H-NMR (CDCl3) d: 0.71 (1H, q, J=12 Hz); 1.24 (3H, t, J=8 Hz), 3.13 (3H, s); 3.34 (3H, s); 3.43 (3H, s); 4.10 (2H, q, J=8 Hz); (1H, m)

MBA (rel. IC50): 1.1
IL-6 dep. prol. (rel. IC50): 1.7

Example 27: 40-O-(2-tolylsulfonamidoethyl)-rapamycin

A solution of 200 mg 40-O-(2-aminoethyl)-rapamycin in 3 mL THF is treated with 0.4 mL pyridine and 390 mg tosyl chloride and the reaction mixture is stirred for 12 h at room temperature. The solution is then poured onto 5 ml of a saturated bicarbonate solution and the aqueous phase is extracted with 2×5 mL ethyl acetate. The combined organic phases are washed with 5 mL of 10% citric acid and 5 mL water. After drying on sodium sulfate the solvent is evaporated and the residue chromatographed on 20 g silica gel, eluting with hexane/ethyl acetate 1/1 to afford the title product as a white foam: MS (FAB) m/z 1133 (100%, M+Na); 1078 (25%, M-MeOH); 1061 (85%, M-(MeOH+H2O))

H-NMR (CDCL3) d: 0.68 (1H, q, J=12 Hz); 2,43 (3H, s); 3,13 (3H, s); 3,35 (3H, s); 3,41 (3H, s); 4.76 (1H, s); 5.85 (1H, t, J=6 Hz); 7.30 (2H, d, J=8 Hz); 7.75 (2H, d, J=8 Hz).

MBA (rel. IC50): 15.9
IL-6 dep. prol. (rel. IC50): 14

Example 28: 40-O-[2-(4',5'-dicarboethoxy-1',2',3'-triazol-1'-yl)-ethyl]-rapamycin 98 mg of 40-O-(2-azidoethyl)-rapamycin and 32 mg diethylacetylene dicarboxylate are suspended in 0.5 ml toluene and heated at 65° C. for 5 h. The reaction mixture is then cooled at room temperature, loaded on 10 g silica gel and eluted with hexane/ethyl acetate 1/1 to afford the title product: MS (FAB) m/z 1175 (20%, M+Na); 1121 (15%, M-MeOH); 1103 (60%, M-(MeOH+H2O))

H-NMR (CDCl3) d: 0.62 (1H, q, J=12 Hz); 1.40 (3H, t, J=8 Hz); 1.42 (3H, t, J=8 Hz); 3.13 (3H, s); 3.25 (3H, s); 3.33 (3H, s)

MBA (rel. IC50): 2.7
IL-6 dep. prol. (rel. IC50): 12

The previous examples may also be made using as starting material instead of rapamycin, 9-deoxo-rapamycin, 26-dihydro rapamycin, or 9-deoxo-, 26-dihydro-rapamycin. Alternatively, and preferably, as described e.g., in example 20, the rapamycin compounds of the above examples may be hydrogenated or reduced, using suitable protecting groups where necessary. The following novel methods for reducing the keto at C9, or hydrogenating the keto at C26 are provided:

Example 29: Removal of keto at C9

A stream of hydrogen sulfide is passed at room temperature through a stirred solution of 3.2 g (3.5 mmol) of rapamycin in 50 ml pyridine and 2.5 ml DMF. The solution turns from colorless to yellow. After two hours, the introduction of hydrogen sulfide is stopped and stirring is continued for five days, during which time the solution turns gradually orange. TLC and HPLC analysis verifies complete consumption of the starting material and the presence of a single new compound. The solution is purged with nitrogen for one hour and concentrated under reduced pressure. The residue is taken up in ethyl acetate, washed with cold 1N HCl solution (3×), saturated sodium bicarbonate solution and saturated brine. The organic layer is dried over anhydrous sodium sulfate and filtered and concentrated under reduced pressure. The residue is taken up in ether and precipitated sulfur is filtered off. Concentration of the ethereal solution followed by column chromatography on silica gel (10:4:1 $CH_2Cl_2$/i-$Pr_2O$/MeOH) yields 9-deoxorapamycin as a colorless foam. The identity of the product is confirmed by nuclear magnetic resonance spectroscopy (NMR), mass spectrometry (MS), and/or infrared spectrosopy (IR). 9-deoxorapamycin is found to exhibit the following characteristic physical data: $^1$H NMR ($CDCL_3$) δ1.61 (3H,d,J=1 Hz, C17-$CH_3$), 1.76 (3H,d,J=1.2 Hz, C29-$CH_3$), 2.42 (1H,d,J=14.5 Hz, H-9), 2.74 (1H,d,J=14.5 Hz, H-9), 3.13 (3H,s,C16-$OCH_3$) 3.5 (3H,s,C27-$OCH_3$), 3.40 (3H,s,C39-$OCH_3$), 5.40 (1H,d,J=10 Hz, H-30), 5.57 (1H, dd,$J_1$=8.6 Hz, $J_2$=15 Hz, H-22), 5.96 (1H,d,J=9 Hz, H-18), 6.09 (1H,d,J=1.7 Hz, 10-OH), 6.15 (1H,dd,$J_1$=10 Hz, $J_2$=15 Hz, H-21), 6.37 (1H,dd,$J_1$=1.5 Hz, $J_2$=5 Hz, H-19), 6.38 (1H,J=9.5 Hz, H-20). $^{13}$C NMR ($CDCl_3$) δ38.5 (C-9), 98.0 (C-10), 170.7 (C-1), 173.0 (C-8), 208.8 (C-32), 216.9 (C-26).

MS(FAB) m/z 922 8[M+Na$^+$]), 899 (M$^+$), 881 ([M-$H_2O$]$^+$), 868 ([M-$OCH_3$]$^+$), 850 ([M-($H_2O$+$OCH_3$)]$^+$).

IR (major peaks)(cm$^{-1}$) 987, 1086, 1193, 1453, 1616, 1717, 1739, 3443.

MBA (rel. IC$_{50}$): 1
MLR (rel. IC$_{50}$): 14
IL-6 dep. prol. (rel. IC$_{50}$): 9

Example 30: Dihydrogenation of keto at C26

To a stirred solution of 421 mg (1.6 mmol) of tetramethylammonium triacetoxyborohydride in 2 ml of acetonitrile is added 2 ml of acetic acid. The resulting mixture is stirred for 30 minutes at room temperature and cooled to −35° C. At this temperature a solution of 180 mg (0.2 mmol) of 9-deoxo-rapamycin in 1 ml of acetonitrile is added and the resulting mixture is allowed to stir for 24 hours. The mixture is quenched with a saturated solution potassium tartrate solution and allowed to warm to room temperature. Stirring is continued until both layers are clear and ethyl acetate is added. The layers are separated and the aqueous layer is extracted twice with ethyl acetate. The resulting organic solution is washed once with a 10% sodium bicarbonate solution and twice with saturated brine, then dried over anhydrous sodium sulfate, filtered and concentrated under reduced pressure. The residue is purified by column chromatography on silica gel (90:10 AcOEt-hexane). As the starting material in this case was 9-deoxorapamycin, the final compound is 9-deoxorapamycin, 26-dihydrorapamycin is produced as a colorless foam, having the following characteristic spectroscopic data: $^1$H NMR ($CDCl_3$) (major isomer) E0.9 (3H,d,J=6.9 Hz, CH$CH_3$), 0.93 (3H,d,J=6.9 Hz, CH$CH_3$), 1.00 (3H,d,J=6.9 Hz, CH$CH_3$), 1.07 (3H,d,J=6.9 Hz, CH$CH_3$), 1.17 (3H,d,J=6.9 Hz, CH$CH_3$), 1.61 (3H,d,J=1 Hz, C17-$CH_3$), 1.73 (3H,d,J=1.2 Hz, C29-$CH_3$), 2.43 (1H,dd,J=4.1 and 16.0 Hz, H-33), 2.46 (1H,dd,J=13.8 Hz, H-9), 2.58 (1H,m,H-25), 2.77 (1H,dd,J=13.8 Hz, H-9), 2.82 (1H,dd,J=8.3 and 16.0 Hz, H-33), 3.17 (1H,dd,J=4.1 and 9.2 Hz, H-27), 3.61 (2H,m, H-14 and H28), 5.19 (1H,ddd,J=4.1, 4.6 and 8.3 Hz, H-34), 5.49 (1H, broad d,J=5.0 Hz, H-2), 5.56 (1H,d,J=9.1 Hz, H-30), 5.75 (1H,dd, J=6.9 and 14.7 Hz, H-22), 5.76 (1H,s,10-OH), 5.99 (1H, broad d,J=9.2 Hz, H-18), 6.10 (1H,m,H-21), 6.36 (2H,m,H-19 and H-20);

MS (FAB) m/z 924 ([M+Na]), 852 ([M-($H_2O$+$CH_3O$)]$^+$).

MBA (rel. IC$_{50}$): 47
MLR (rel. IC$_{50}$): 134
IL-6 dep. prol. (rel. IC$_{50}$): 78

26-dihydrorapamycin is prepared in the same manner, using rapamycin in place of 9-deoxorapamycin. This product has the following characteristic spectroscopic data: $^{13}$C-NMR ($CDCl_3$) (major isomer) d=208.3 (C-32); 194.0 (C-9); 169.3 (C-1); 166.6 (C-8); 140.9 (C-22); 136.5 (C-29); 136.2 (C-17); 133.5 (C-20); 129.1 (C-21); 128.7 (C-18); 126.2 (C-30); 125.3 (C-19); 98.6 (C-10); 84.4 (C-39); 83.9 (C-16; 81.6 (C-27); 75.4 (C-34); 74.3 (C-28); 73.9 (C-40); 72.9 (C-26); 67.4 (C-14); 59.1 (27-O$CH_3$); 56.6 (39-O$CH_3$); 55.9 (16-O$CH_3$); 51.3 (C-2); 46.8 (C-31); 44.3 (C-6); 40.4

(C-33); 40.4 (C-25); 39.5 (C-24); 38.8 (C-15); 38.0 (C-36); 34.3 (C-23); 34.2 (C-38); 33.5 (C-11); 33.3 (C-37); 33.2 (C-35); 31.5 (C-42); 31.3 (C-41); 30.9 (C-13); 27.1 (C-12); 27.0 (C-3); 25.2 (C-5); 21.4 (23-$\underline{C}H_3$); 20.7 (C-4); 17.3 (11-$\underline{C}H_3$); 16.1 (31-$\underline{C}H3$); 15.9 (35-$\underline{C}H_3$); 14.4 (25-$\underline{C}H_3$); 14.2 (29-$\underline{C}H_3$); 10.3 (17-$\underline{C}H_3$).

MS (FAB) m/z: 884 (M-$OCH_3$, 35%); 866 (M-[$OCH_3$+$H_2O$], 100%; 848 (M-[$OCH_3$+2 $H_2O$], 40%).

MBA (rel. $IC_{50}$): 1.7
MLR (rel. $IC_{50}$): 1
IL-6 dep. prol. (rel. $IC_{50}$): 7.5

We claim:

1. A compound of the formula

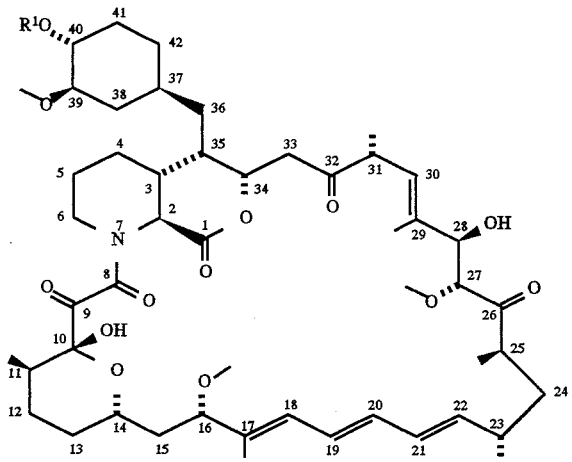

wherein $R^1$ is hydroxy($C_{1-6}$)alkyl or hydroxy($C_{1-3}$)alkoxy($C_{1-3}$)alkyl.

2. A compound according to claim 1 in which $R^1$ is hydroxy($C_{1-3}$)alkyl or hydroxy($C_{1-3}$)alkoxy($C_{1-3}$)alkyl.

3. A compound according to claim 1 in which $R^1$ is hydroxy($C_{1-3}$)alkyl.

4. A compound according to claim 1 in which $R^1$ is hydroxy($C_{1-3}$)alkoxy($C_{1-3}$)alkyl.

5. The compound according to claim 1 which is 40-O-(3-hydroxypropyl)-rapamycin.

6. The compound according to claim 1 which is 40-O-[2-(2-hydroxyethoxy)ethyl]-rapamycin.

7. A pharmaceutical composition comprising a therapeutically effective amount of a compound according to claim 1 and a pharmaceutically acceptable carrier therefor.

8. A method of inducing an immunosuppressant effect in a subject in need of immunosuppression, which comprises administering to said subject an immunosuppressant effective amount of a compound according to claim 1.

9. A method of preventing allograft rejection in a subject in need of such treatment, which comprises administering to said subject a compound according to claim 1 in an amount effective to prevent allograph rejection.

10. The compound according to claim 1 which is 40-O-(3-hydroxyethyl)-rapamycin.

* * * * *

UNITED STATES PATENT AND TRADEMARK OFFICE
CERTIFICATE OF CORRECTION

PATENT NO. : 5,665,772
DATED : September 9, 1997
INVENTOR(S) : Sylvain Cottens and Richard Sedrani It is certified that error appears in the above-identified patent and that said Letters Patent is hereby corrected as shown below:

Claim 10, lines 1-2, delete "40-O-(3-hydroxyethyl)-rapamycin" and replace it with -- 40-O-(2-hydroxyethyl)-rapamycin --.

Signed and Sealed this

Thirtieth Day of June, 1998

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

| | | |
|---|---|---|
| PATENT NO. | : 5,665,772 | Page 1 of 1 |
| APPLICATION NO. | : 08/416673 | |
| DATED | : September 9, 1997 | |
| INVENTOR(S) | : Cottens et al. | |

It is certified that error appears in the above-identified patent and that said Letters Patent is hereby corrected as shown below:

In the Claims

Claim 9, line 27, "allograph" should be changed to --allograft--.

Signed and Sealed this
Second Day of June, 2015

Michelle K. Lee
*Director of the United States Patent and Trademark Office*

UNITED STATES PATENT AND TRADEMARK OFFICE
CERTIFICATE OF CORRECTION

PATENT NO. : 5,665,772  
APPLICATION NO. : 08/416673  
DATED : September 9, 1997  
INVENTOR(S) : Sylvain Cottens et al.

Page 1 of 1

It is certified that error appears in the above-identified patent and that said Letters Patent is hereby corrected as shown below:

IN THE CLAIMS

Claim 1, lines 15-30, delete the formula and replace it with

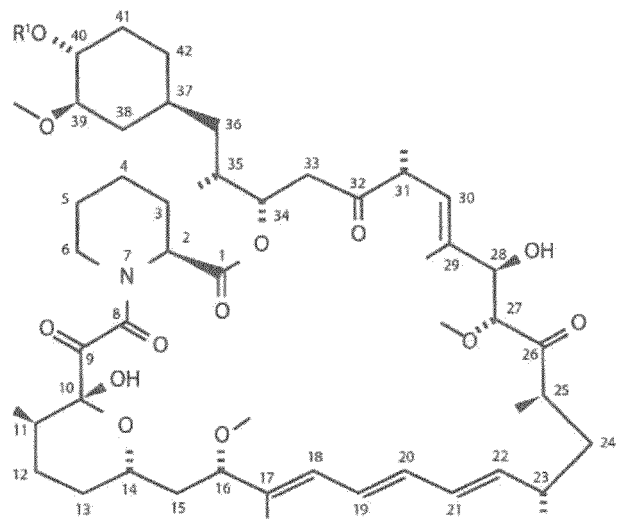

Signed and Sealed this  
Ninth Day of February, 2016

Michelle K. Lee  
*Director of the United States Patent and Trademark Office*